United States Patent [19]

Sumita et al.

[11] Patent Number: 4,919,751
[45] Date of Patent: Apr. 24, 1990

[54] METHOD FOR PRODUCING POROUS SINTERED APATITE MATERIAL

[75] Inventors: Masaya Sumita; Hitoshi Akiyama, both of Tokyo, Japan

[73] Assignee: Asahi Kogaku Kogyo Kabushiki Kaisha, Tokyo, Japan

[21] Appl. No.: 304,446

[22] Filed: Feb. 1, 1989

[30] Foreign Application Priority Data

Feb. 1, 1988 [JP] Japan .................................. 63-21691
May 31, 1988 [JP] Japan ................................ 63-134188

[51] Int. Cl.$^5$ ........................ B44C 1/22; C03C 15/00; C03C 25/06; C04B 35/00
[52] U.S. Cl. .................................. 156/646; 156/654; 501/1; 501/80; 106/35
[58] Field of Search ...................... 501/1, 80; 106/35; 156/646, 654

[56] References Cited

U.S. PATENT DOCUMENTS 2,215,039  9/1940  Hood et al. .......................... 65/32.5
3,843,341  10/1974 Hammel et al. ..................... 502/202
4,687,675  8/1987  Nakano et al. ........................... 427/2

Primary Examiner—Mark L. Bell
Assistant Examiner—Anthony J. Green
Attorney, Agent, or Firm—Sughrue, Mion, Zinn, Macpeak & Seas

[57] ABSTRACT

A method for producing a porous sintered apatite material comprising the steps of:

sintering a calcium-excess apatite at 800° C. or more so as to form a sintered apatite material having a calcium oxide content of from 0.5 to 60 wt % by phase separation of calcium oxide; and removing the calcium oxide from the sintered apatite material so as to form a porous sintered apatite material.

11 Claims, 1 Drawing Sheet

METHOD FOR PRODUCING POROUS SINTERED APATITE MATERIAL

FIELD OF THE INVENTION

The present invention relates to a method for producing porous sintered apatite material which is advantageously used as an artificial tooth root, an artificial bone, etc.

BACKGROUND OF THE INVENTION

As a method for producing a porous apatite material, the foaming method (as described, e.g., in *Philips Tech. Rev.*, vol. 37, p234–236 (1977)) and the thermal decomposition method (as described, e.g., in JP-A-57-4710 and JP-A-58-129087) have been conventionally known. (The term "JP-A" as used herein means an "unexamined published Japanese patent application")

In the foaming method, a foaming agent such as hydrogen peroxide or the like is added to a calcium phosphate slurry, and the slurry is dried and foams so as to produce a porous material. However, the pore diameter and the porosity are difficult to control in this method.

In the thermal decomposition method, thermally decomposable particles such as organic polymer resin particles or the like are mixed with a calcium phosphate slurry, and after molding, the resin particles are burnt out by heating so as to produce a porous material; or a polyurethane foam material is impregnated with a calcium phosphate slurry, and the polyurethane foam material is burnt out by heating so as to produce a porous material. However, toxic gases, which are harmful for environment pollution, are generated upon decomposing the organic polymer resin or the poilyurethane foam material.

SUMMARY OF THE INVENTION

An object of the present invention is to provide a simple method for producing a porous sintered apatite material which is advantageously used as an artificial tooth root, an artificial bone, etc. in which the pore diameter and the porosity can easily be controlled and no toxic substance is generated in the production process.

Other objects and effects of the present invention will be apparent from the following description.

The above objects of the present invention have been attained by a method for producing a porous sintered apatite material comprising the steps of:

sintering a calcium-excess apatite at 800° C. or more so as to form a sintered apatite material having a calcium oxide content of from 0.5 to 60 wt % by phase separation of calcium oxide; and removing the calcium oxide from the sintered apatite material so as to form a porous sintered apatite material.

DETAILED DESCRIPTION OF THE INVENTION

Figure 1:
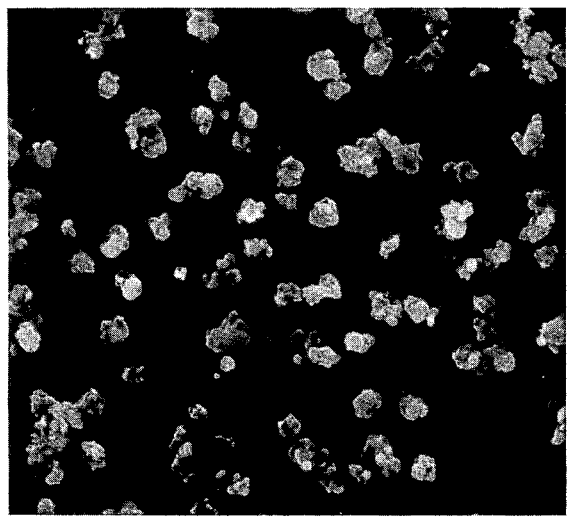
FIG. 1 shows a scanning electron micrograph of the surface structure of the sintered material produced in Example 1 which is not washed with water.

When calcium-excess apatite is sintered at a temperature of 800° C. or more, calcium oxide is phase-separated and a mixture of apatite and calcium oxide is formed.

Calcium-excess apatite used in the present invention as a starting material has a Ca/P ratio of more than 1.67 and can be prepared by conventional methods for preparing apatite while a calcium compound is used excessively, or a phosphate compound (including phosphoric acid) is used in an amount less than that required for producing apatite having a Ca/P ratio of 1.67. The calcium-excess apatite thus-obtained can be molded by conventional methods such as by drying a slurry of calcium-excess apatite by a conventional method and then dry-molding, or by wet-molding the slurry as it is.

The resulting calcium-excess apatite is sintered at 800° C. or more, preferably from 800° to 1,500° C., more preferably from 1,000° to 1,300° C., so as to obtain a sintered apatite material having a calcium oxide content of from 0.5 to 60 wt %, preferably from 0.5 to 30 wt %, by phase separation of calcium oxide. The calcium oxide content can easily be controlled by changing the Ca/P ratio of the starting calcium-excess apatite which is simply proportional to the calcium oxide content. In this material, calcium oxide is considered to be contained as a discontinuous phase uniformly distributed in the apatite as a matrix when the calcium oxide content is relatively small, and with increase of the calcium oxide content, calcium oxide grains in the material may be joined to form a partially continuous phase.

If the sintering temperature is less than 800° C., the amount of calcium oxide thus formed is too small and the strength of the sintered material is also too small. If the calcium oxide content is less than 0.5 wt %, a porosity which is enough for practical use cannot be attained because of less amount of calcium oxide. If the calcium oxide content is more than 60 wt %, the strength of the final product is extremely small because the amount of the matrix apatite material is too small.

The calcium oxide in the resulting sintered apatite material can be removed by any suitable method, for example, (1) by washing the sintered apatite material with water, (2) contacting the sintered apatite material to water vapor having a high temperature and a high pressure in an autoclave, or (3) immersing or washing the sintered apatite material into or with at least one substance selected from the group consisting of a ketone, a sugar, a sugaralcohol, a polyhydric alcohol and a chelating agent, or an aqueous solution of these substances.

In the removing step, the mechanism of removal of calcium oxide would depend on the removing method employed. Calcium oxide often reacts with water to form calcium hydroxide. Because calcium hydroxide is not easily soluble in water but has far higher solubility in water than apatite, calcium hydroxide can be removed from the apatite matrix by the above methods for example. Also, calcium oxide as it is may drop off from the apatite matrix.

When the sintered apatite material is washed with water (1), water as used and the temperature thereof is not limited. Water other than pure water such as tap water can be used, and the washing step can be conducted at room temperature.

When the sintered apatite material is contacted with water vapor having a high temperature and a high pressure in an autoclave (2), a high-pressure water vapor sterilizer which is conventionally employed can be used as an autoclave, and the water vapor preferably has a temperature of from 120° to 132° C. and a pressure of about 2 kg/cm².

When the sintered apatite material is immersed into or washed with at least one substance selected from the group consisting of a ketone, a sugar, a sugaralcohol, a polyhydric alcohol and a chelating agent, or an aqueous solution of these substances (3), any of ketones, sugars, sugaralcohols, polyhydric alcohols and chelating agents that can dissolve calcium oxide or calcium hydroxide, or can accerelate dissolving of calcium oxide or calcium hydroxide in water may be used.

Examples of the ketone include cyclopentanone and cyclohexanone. Examples of the sugar include monosaccharide such as glucose and fructose, oligosaccharide such as saccharose, maltose and lactose. Examples of the sugaralcohol include xylitol and sorbitol. Examples of the polyhydric alcohol include glycerin and pentaerithrytol. Examples of the chelating agent include EDTA (ethylenediaminetetraacetic acid) and a salt thereof (such as a sodium salt) and NTA (nitrilotriacetic acid) and a salt thereof (such as a sodium salt).

Among the above substances, an aqueous solution of glucose, fructose and/or saccharose is preferably used.

The substance selected from a ketone, a sugar, a sugaralcohol, a polyhydric alcohol and a chelating agent may be used alone or in combination of two or more of them. These substances may be used as they are or in the form of an aqueous solution. When these substances are used as an aqueous solution, the concentration of these substances depends on the type of the substance, and is preferably 10 wt % or more, and more preferably 20 wt % or more.

In the removing step of the present invention, it is preferred to use the above described substance selected from a ketone, a sugar, a sugaralcohol, a polyhydric alcohol and a chelating agent, and an aqueous solution of them, because calcium oxide or calcium hydroxide can easily be removed in comparison to the case using water.

In the removing step of the present invention, removal of calcium oxide occurs from the surface region to the interior region of the material. Thus, a porous surface is firstly formed and the thickness of the porous surface increases with progress of the removing step. The period of time for removing step is not limited and depends on the method employed.

Accordingly, the porous sintered apatite material produced by the present invention is porous at least in the surface region thereof. A material which is porous only in a surface region having a thickness of from several tens to 100 μm can practically be used as an artificial tooth root, an artificial bone or the like. The thickness of the porous surface region can easily be controlled by the conditions in the removing step.

In the present invention, the pore diameter and the porosity can easily be controlled by changing the size and the amount of the particles (i.e., the discontinuous phase) of calcium oxide in the sintered apatite material. That is, when the material is sintered at a higher temperature, a larger pore size can be obtained. When the amount of calcium oxide is larger, the higher porosity can be obtained.

The present invention will be explained in more detail by referring to the following examples, but the present invention is not construed as being limited thereto.

EXAMPLE 1

A calcium-excess apatite slurry was prepared by reacting an aqueous phosphoric acid solution and a calcium hydroxide dispersion by the conventional method while the amount of the aqueous phosphoric acid solution was less than the stoichiometric amount for producing apatite. The resulting calcium-excess apatite slurry was powdered by spray drying, and was formed into a powder compressed body by using a hydrostatic press of 196 MPa. The powder compressed body obtained was sintered at 1,060° C. for 4 hours to produce a sintered material which was found to have 0.6 wt % of calcium oxide thus phase separated. The scanning electron micrograph of the surface stracture of the sintered material is shown in FIG. 1.

Figure 2:
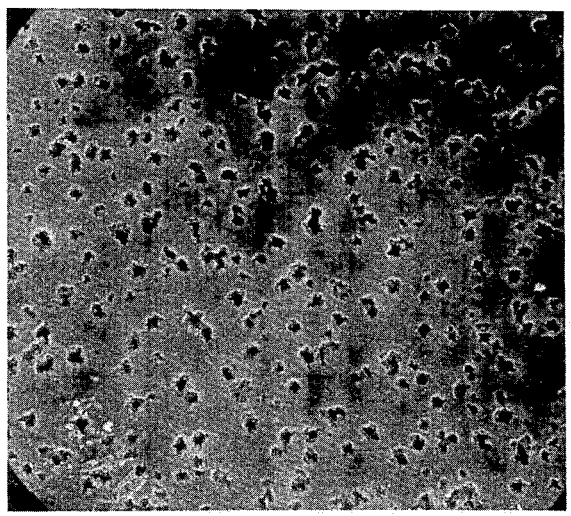
FIG. 2 shows a scanning electron micrograph of the surface structure of the porous sintered material produced in Example 1 which has been washed with water.

The sintered material was washed with water at room temperature for 30 minutes so as to obtain a porous material. The average pore diameter of the porous apatite material was 20 μm. The scanning electron micrograph of the surface stracture of the porous material is shown in FIG. 2.

EXAMPLE 2

A sintered apatite material having a calcium oxide content of 0.6 wt % was prepared in the same manner as in Example 1.

The sintered material was washed with a 20 wt % aqueous solution of glucose for about 15 minutes to obtain a porous material. The average pore diameter of the porous apatite material was 20 μm.

EXAMPLE 3

A sintered apatite material having a calcium oxide content of 0.6 wt % was prepared in the same manner as in Example 1.

The sintered material was washed with a 60 wt % aqueous solution of glycerin for about 20 minutes to obtain a porous material. The average pore diameter of the porous apatite material was 20 μm.

EXAMPLE 4

A sintered apatite material having a calcium oxide content of 0.6 wt % was prepared in the same manner as in Example 1.

The sintered material was washed with a mixture of methyl ethyl ketone and water (mixing ratio: 9/1 by weight) for about 15 minutes to obtain a porous material. The average pore diameter of the porous apatite material was 20 μm.

EXAMPLE 5

A sintered apatite material having a calcium oxide content of 0.6 wt % was prepared in the same manner as in Example 1.

The sintered material was washed with a 20 wt % aqueous solution of sorbitol for about 20 minutes to obtain a porous material. The average pore diameter of the porous apatite material was 20 μm.

EXAMPLE 6

A sintered apatite material having a calcium oxide content of 0.6 wt % was prepared in the same manner as in Example 1.

The sintered material was washed with a 10 wt % aqueous solution of disodium ethylenediaminetetraacetate for about 15 minutes to obtain a porous material.

The average pore diameter of the porous apatite material was 20 μm.

As described above, accoding to the present invention, a porous sintered apatite material can easily be obtained without generation of toxic substance while the pore diameter and the porosity can easily be controlled. Furthermore, by using at least one substance selected from the group consisting of a ketone, a sugar, a sugaralcohol, a polyhydric alcohol and a chelating agent, or an aqueous solution of these substance, a porous sintered apatite material can further easily be obtained in comparison to the case using only water.

While the invention has been described in detail and with reference to specific embodiments thereof, it will be apparent to one skilled in the art that various changes and modifications can be made therein without departing from the spirit and scope thereof.

What is claimed is:

1. A method for producing a porous sintered apatite material comprising the steps of:
   sintering a calcium-excess apatite at a temperature of at least 800° C. so as to form a sintered apatite material having a calcium oxide content of from 0.5 to 60 wt % by phase separation of calcium oxide; and
   removing said calcium oxide from said sintered apatite material by contacting the sintered apatite material with a liquid or a vapor so as to form a porous sintered apatite material.

2. A method for producing a porous sintered apatite material as claimed in claim 1, wherein said sintered apatite material has a calcium oxide content of from 0.5 to 30 wt %.

3. A method for producing a porous sintered apatite material as claimed in claim 1, wherein said removing step comprises the step of: washing said sintered apatite material having a calcium oxide content of from 0.5 to 60 wt % with water.

4. A method for producing a porous sintered apatite material as claimed in claim 1, wherein said removing step comprises the step of: contacting said sintered apatite material having a calcium oxide content of from 0.5 to 60 wt % with water vapor having a high temperature and a high pressure in an autoclave.

5. A method for producing a porous sintered apatite material as claimed in claim 4, wherein said water vapor has a temperature of from 120° to 132° C. and a pressure of about 2 kg/cm$^2$.

6. A method for producing a porous sintered apatite material as claimed in claim 1, wherein said removing step comprises the step of: immersing or washing said sintered apatite material having a calcium oxide content of from 0.5 to 60 wt % into or with at least one substance selected from the group consisting of a ketone, a sugar, a sugaralcohol, a polyhydric alcohol and a chelating agent, or an aqueous solution of said substance.

7. A method for producing a porous sintered apatite material as claimed in claim 6, wherein said removing step comprises the step of: immersing or washing said sintered apatite material having a calcium oxide content of from 0.5 to 60 wt % into or with an aqueous solution of at least one substance selected from the group consisting of glucose, fructose and saccharose.

8. A method for producing a porous sintered apatite material as claimed in claim 1, wherein said calcium-excess apatite is sintered from 800° to 1,500° C.

9. A method for producing a porous sintered apatite material as claimed in claim 8, wherein said calcium-excess apatite is sintered from 1,000° to 1,300° C.

10. A method for producing a porous sintered apatite material as claimed in claim 6, wherein said removing step comprises the step of: immersing or washing said sintered apatite material having a calcium oxide content of from 0.5 to 60 wt % into or with an aqueous solution of said substance having a concentration of 10 wt % or more.

11. A method for producing a porous sintered apatite material as claimed in claim 10, wherein said removing step comprises the step of: immersing or washing said sintered apatite material having a calcium oxide content of from 0.5 to 60 wt % into or with an aqueous solution of said substance having a concentration of 20 wt % or more.

* * * * *